United States Patent [19]

Persico et al.

[11] Patent Number: 5,792,616
[45] Date of Patent: Aug. 11, 1998

[54] ANTIBODIES TO HUMAN CRIPTO PROTEIN

[75] Inventors: Maria G. Persico, Naples, Italy; David S. Salomon, Germantown, Md.

[73] Assignee: The United States of America, Washington, D.C.

[21] Appl. No.: 463,616

[22] Filed: Jun. 5, 1995

Related U.S. Application Data

[62] Division of Ser. No. 337,911, Nov. 10, 1994, Pat. No. 5,654,140, which is a continuation of Ser. No. 947,315, Sep. 28, 1992, abandoned, which is a division of Ser. No. 530,165, May 29, 1990, Pat. No. 5,256,643.

[51] Int. Cl.$^6$ .......................... C07K 16/30; G01N 33/53
[52] U.S. Cl. .................. 435/7.21; 435/7.23; 530/387.1; 530/387.9; 530/388.2; 530/388.8; 530/388.85; 530/389.7; 530/389.1
[58] Field of Search .................. 530/387.9, 388.2, 530/388.8, 388.85, 389.7, 389.1; 435/7.1, 240, 27, 7.21, 7.23

[56] References Cited

PUBLICATIONS

Ciccodicola, EMBO 8:1987–1991, 1989.
Kobrin, J. Biol Chem 261:14414–14419, 1986.
Dono, Am. J. Hum. Genet. 49:555–565, 1991.

*Primary Examiner*—Lila Feisee
*Assistant Examiner*—Nancy A. Johnson
*Attorney, Agent, or Firm*—Townsend and Townsend and Crew

[57] ABSTRACT

A new human gene designated as "CRIPTO" gene has been identified and cloned. CRIPTO gene products and derivatives thereof have been obtained and various utilities of the same have been described. Polyclonal and monoclonal antibodies to the human CRIPTO protein have been described. Association of CRIPTO gene with cancers, such as colorectal cancer and breast carcinoma, has been indicated.

4 Claims, 8 Drawing Sheets

```
                                                             60
GGAGAATCCCCGGAAAGGCTGAGTCTCCAGCTCAAGGTCAAAACGTCCAAGGCCGAAAGC

120
CCTCCAGTTTCCCCTGGACGCCTTGCTCCTGCTTCTGCTACGACCTTCTGGGGAAAACGA

180
ATTTCTCATTTTCTTCTTAAATTGCCATTTTCGCTTTAGGAGATGAATGTTTTCCTTTGG

240
CTGTTTTGGCAATGACTCTGAATTAAAGCGATGCTAACGCCTCTTTTCCCCCTAATTGTT

300
AAAAGCTATGGACTGCAGGAAGATGGCCCGCTTCTCTTACAGTGTGATTTGGATCATGGC
         M   D   C   R   K   M   A   R   F   S   Y   S   V   I   W   I   M   A

360
CATTTCTAAAGTCTTTGAACTGGGATTAGTTGCCGGGCTGGGCCATCAGGAATTTGCTCC
  I   S   K   V   F   E   L   G   L   V   A   G   L   G   N   Q   E   F   A   R

420
TCCATCTCGGGGATACCTGGCCTTCAGAGATGACAGCATTTGGCCCCAGGAGGAGCCTGC
  P   S   R   G   Y   L   A   F   R   D   D   S   I   W   P   Q   E   E   P   A

480
AATTCGGCCTCGGTCTTCCCAGCGTGTGCCGCCCATGGGGATACAGCACAGTAAGGAGCT
  I   R   P   R   S   S   Q   R   V   P   P   M   G   I   Q   H   S   K   E   L

540
AAACAGAACCTGCTGCCTGAATGGGGGAACCTGCATGCTGGGGTCCTTTTGTGCCTGCCC
  N   R   T   C   C   L   N   G   C   T   M   L   G   S   F   C   A   C   P

600
TCCCTCCTTCTACGGACGGAACTGTGAGCACGATGTGCGCAAAGAGAACTGTGGGTCTGT
  P   S   F   Y   G   R   N   C   E   H   D   V   R   K   E   N   C   G   S   V
```

*FIG. 1A.*

```
                                                                660
GCCCCATGACACCTGGCTGCCCAAGAAGTGTTCCCTGTGTAAATGCTGGCACGGTCAGCT
  P   H   D   T   W   L   P   K   K   C   S   L   C   K   C   W   H   G   Q   L
                                                                720
CCGCTGCTTTCCTCAGGCATTTCTACCCGGCTGTGATGGCCTTGTGATGGATGAGCACCT
  R   C   F   P   Q   A   F   L   P   G   C   D   C   L   V   M   D   E   H   L
                                                                780
CGTGGCTTCCAGGACTCCAGAACTACCACCGTCTGCACGTACTACCACTTTTATGCTAGT
  V   A   S   R   T   P   E   L   P   P   S   A   R   T   T   T   F   M   L   V
                                                                840
TGGCATCTGCCTTTCTATACAAAGCTACTATTAATCGACATTGACCTATTTCCAGAAATA
  G   I   C   L   S   I   Q   S   Y   Y
                                                                900
CAATTTTAGATATCATGCAAATTTCATGACCAGTAAAGGCTGCTGCTACAATGTCCTAAC
                                                                960
TGAAAGATGATCATTTGTAGTTCCCTTAAAATAATGAATACAATTTCCAAAATGGTCTCT
                                                                1020
AACATTTCCTTACAGAACTACTTCTTACTTCTTTGCCCTGCCCTCTCCCAAAAAACTACT
                                                                1180
TCTTTTTTCAAAAGAAAGTCAGCCATATCTCCATTGTGCCTAAGTCCAGTGTTTCTTTTT
                                                                1140
TTTTTTTTTTTTTGAGACGCAGTCTCACTCTGTCACCCAGGCTGGACTGCAATGACGCGAT
                                                                1200
CTTGGTTCACTGCAACCTCCGCATCCGGGGTTCAAGCCATTCTCCTGCCTAAGCCTCCCA
                                                                1260
AGTAACTGCGATTACAGGCATGTGTCACCATGCCCAGCTAATTTTTTTGTATTTTAGTAG
                                                                1320
AGATGGGGGTTTCACCATATTGGCCAGTCTGGTCTCGAACTCTGACCTTGTGATCCATCG
```

FIG. 1B.

```
                                                                      1380
ATCAGCCTCTCGAGTGCTGAGATTACACACGTGAGCAACTGTGCAAGGCCTGGTGTTTCT
                                                                      1440
TGATACATGTAATTCTACCAAGGTCTTCTTAATATGTTCTTTTAAATGATTGAATTATAT
                                                                      1500
CTTCAGATTATTGGAGACTAATTCTAATGTGGACCTTAGAATACAGTTTTGAGTAGAGTT
                                                                      1560
GATCAAAATCAATTAAAATAGTCTCTTTAAAAGGAAAGAAAACATCTTTAAGCCGAGGAA
                                                                      1620
CCAGAGTGCTGAAGGAATGCAAGTCCATCTGCGTGTGTGCAGGGAGACTGGGTAGCAAAG
                                                                      1680
AGGAAGCAAATAGAAGAGACAGGTTGAAAAACAAAATGGGTTACTTGATTGGTGATTAGC
                                                                      1740
TGGTGGTAGAGAAGCAAGTAAAAAGGCTAAATGGAAGGGCAAGTTTCCATCATCTATAGA
                                                                      1800
AAGCTATATAAGACAAGAACTCCCCTTTTTTTCCCAAAGGCATTATAAAAAGAATGAAGC
                                                                      1860
CTCCTTAGAAAAAAAATTATACCTCAATGTCCCCAACAAGATTGCTTAATAAATTGTCTT
                                                                      1920
TCCTCCAAGCTATTCAATTCTTTTAACTGTTGTAGAAGACAAAATGTTCACAATATATTT
                                                                      1980
AGTTGTAAACCAAGTGATCAAACTACATATTGTAAAGCCCATTTTTAAAATACATTGTAT

ATATGTGTATGCACAGTAAAAATGGAAACTATATTGACCTAAAAAAAAAAAAA
```

SW480
SW620 
JVC
CBS 
HCT116
Moser
MoserR

Geo

HCT116

ANTIBODIES TO HUMAN CRIPTO PROTEIN

This application is a division of application Ser. No. 08/337,911, filed Nov. 10, 1994, now U.S. Pat. No. 5,654, 140 which is a FWC continuation of U.S. divisional application Ser. No. 07/947,315, filed Sep. 28, 1992, now abandoned, which is a divisional of U.S. application Ser. No. 07/530,165, filed May 29, 1990, now U.S. Pat. No. 5,256, 643, all of which are hereby incorporated in their entirety by reference.

BACKGROUND OF THE INVENTION

The present invention is related generally to the isolation and cloning of genes and obtaining products encoded by the gene. More particularly, the present invention is related to the isolation, cloning, sequencing and expression of the human CRIPTO gene and producing an isolated, substantially pure gene products including mRNA and recombinant CRIPTO protein.

Figure 1A:
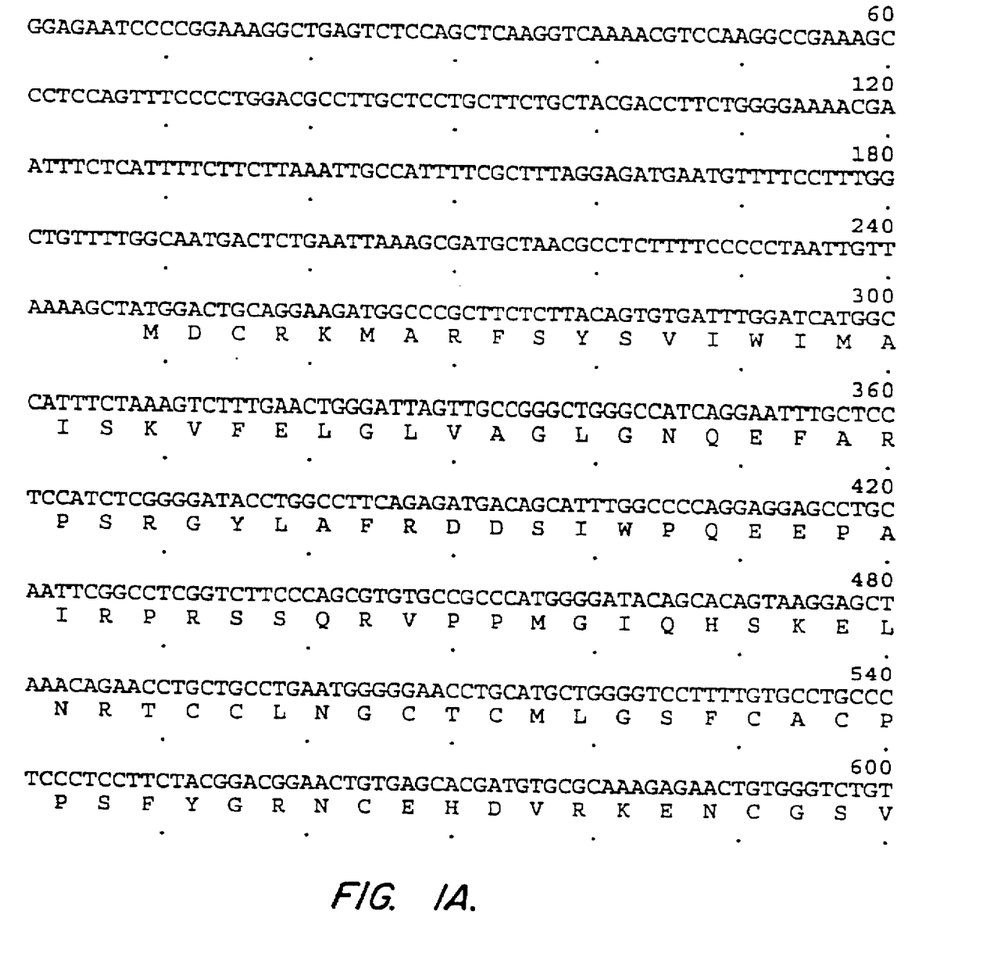
FIG. 1 shows the nucleotide sequence of human CRIPTO gene cDNA and the corresponding amino acid sequence.
Figure 1B:
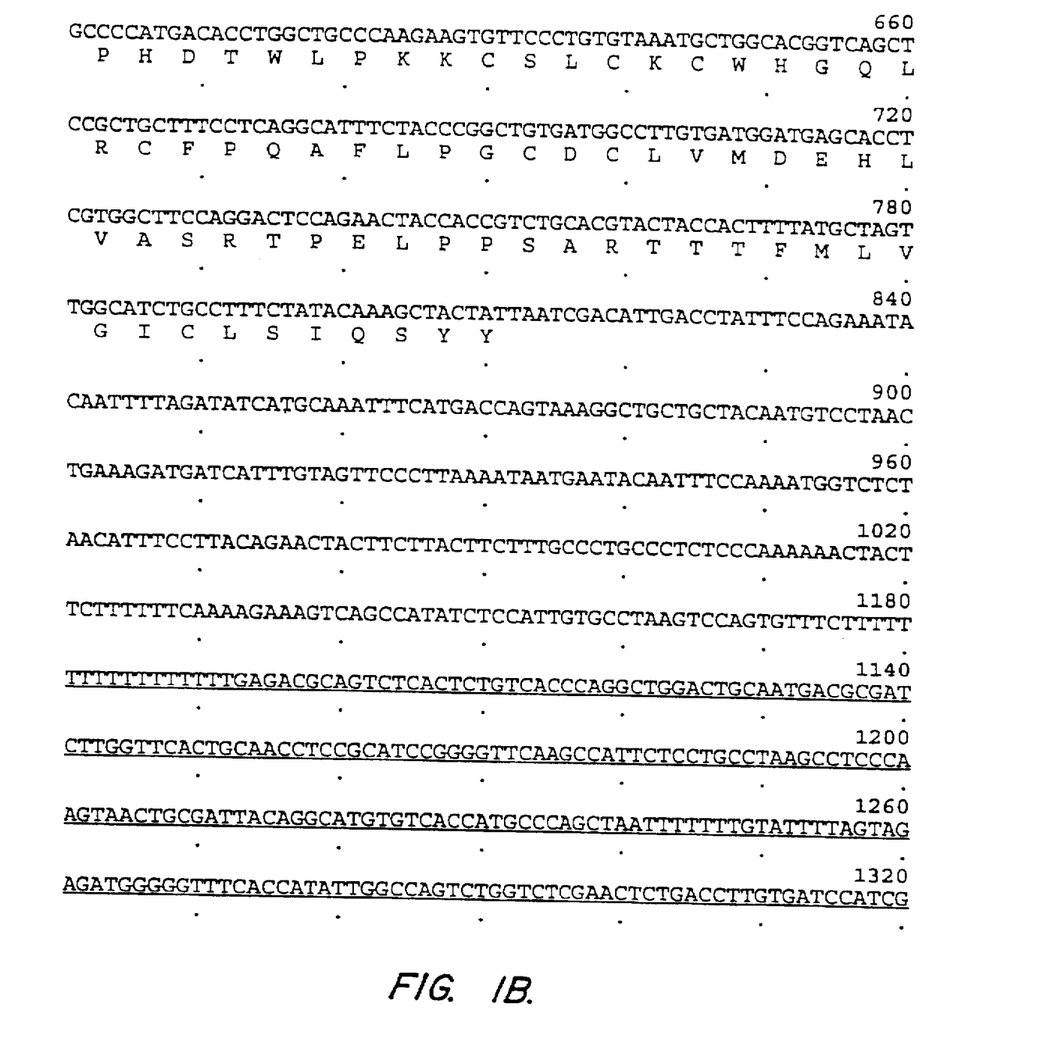
Figure 1C:
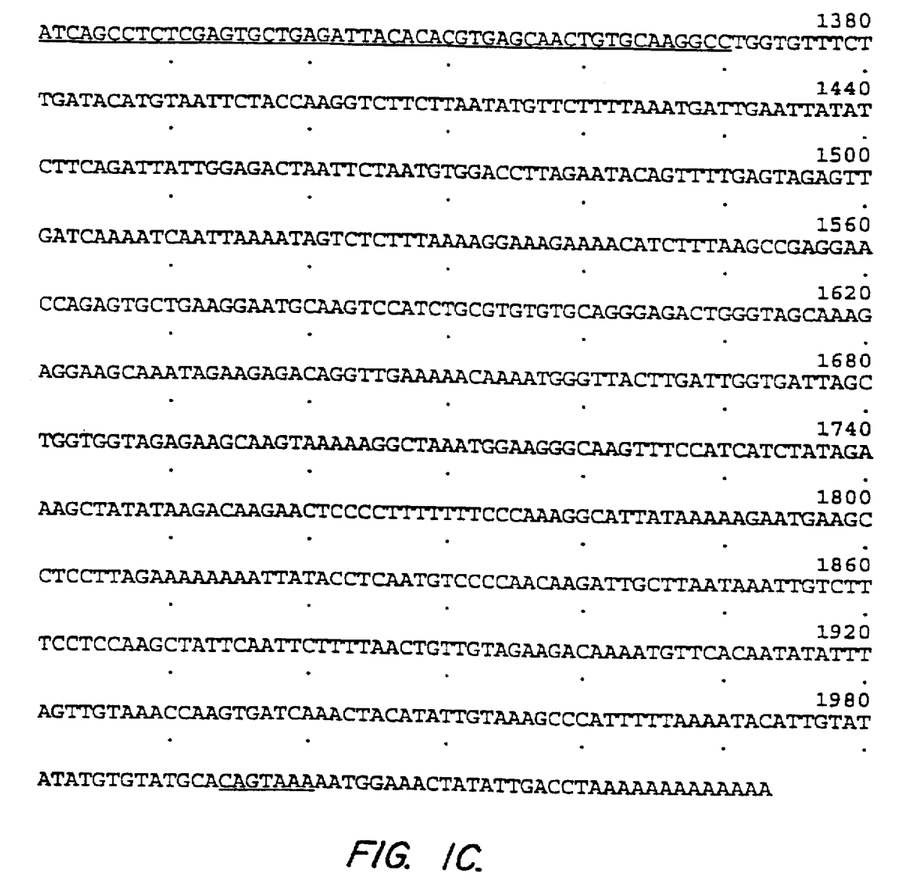

"CRIPTO" is a new human gene which has never been previously described. The gene has been isolated, cloned and completely sequenced. FIG. 1 shows the nucleotide sequence of the CRIPTO cDNA and the amino acid sequence deduced therefrom. FIG. 1 also shows the amino acid sequence of the natural CRIPTO protein and FIG. 2 the amino acid sequence of the recombinant E. coli derived CRIPTO protein.

DETAILED DESCRIPTION OF THE INVENTION

Isolation and Characterization of Human CRIPTO cDNA

In screening $3 \times 10^7$ independent clones of a human teratocarcinoma NT2D1 cell line cDNA library that was expressed in λgt10 and that was originally derived from NT2D1 poly(A)+RNA to isolate a full-length glucose-6-phosphate dehydrogenase (G6Pd) cDNA, 16 different clones were identified (Persico et al., *Nucleic Acid Research*, 14:2511–2522, 1986). One of these clones exceeded the expected size for the G6PD mRNA. Restriction mapping and sequencing showed that the aberrant cDNA which was approximately 5 kb in length to be a composite of two separate coding entities. A nucleotide segment of 2.8 kb corresponded to G6PD while the remaining 2.2 kb fragment (16B6 cDNA) had no relationship to the G6PD gene. The 16B6 cDNA fragment was used to probe the same NT2D1 cDNA library to isolate a full-length cDNA.

From several positive clones, 10 clones were isolated and subcloned into pUC18 after EcoR1 digestion. Analysis by restriction enzyme mapping and agarose gel electrophoresis demonstrated that the size of the various cDNA inserts varied from about 0.9 Kb to 2.0 Kb. The two largest cDNA clones, p3B2 and p1C1, and the shortest p2B3, were sequenced by the Sanger method. The complete nucleotide sequence has been deposited in the EMBL Gene Data Bank.

The open reading frame of 564 base pairs codes for a protein of 188 amino acids in length (FIG. 1). Proteolytic cleavage sites are present in this protein designated CRIPTO at V-A (amino acid residues 28-29 and 159-160), R-K (residues 111-112), K-K (residues 126-127) and R-T-T-T (residues 171-174). One potential asparagine glycosylation sequence (Asn-Arg-Thr) is present at residues 79-81.

Production and Purification of Recombinant CRIPTO Protein in *E. Coli*

The buffers are prepared as follows:

Buffer A: 25% sucrose, 10 mM Tris-HCl (pH 8.0), 1mM EDTA, 150 mM NaCl and 10 µg lysozyme.

Buffer B: 10 mM Tris-HCl (pH 7.6), 1mM EDTA and 0.5% Triton X-100.

Buffer C: 0.1% SDS, 0.05M Tris-HCl (pH 8.0), 0.1mM EDTA, 5 mM DTT and 0.20M NaCl.

1. Grow an inoculum of suitably competent strain of bacteria in LB broth containing 100 µg/ml of ampicillin overnight at about 32° C.

2. Dilute the bacterial culture 100-fold in LB broth and grow at 32° C. until $OD_{600}$ reaches 0.2.

3. Shift the bacterial culture to 44° C. for 20 minutes and then to 42° C. for 4 hours until $OD_{600}$ reaches 1.7.

4. Spin 50 ml of the bacterial culture at 5,000 g for 10 minutes at 4° C. and resuspend the bacterial pellet in 10 ml LB broth at room temperature (RT).

5. To 10 ml of frozen buffer A add 10 ml of bacterial suspension and defrost at RT prior to incubation for 15 minutes at 37° C.

6. Spin at 27,000 g for 10 minutes at 4° C.

7. Resuspend the pellet in 3 ml of buffer B and spin at 15000 rpm for 15 minutes at 4° C.

8. Repeat step #7 three times, saving the supernatant each time.

9. Sonicate the final spheroplast suspension 6 times for 30 seconds at 40 watts.

10. Divide into 4 Eppendorff tubes and spin at RT in a microfuge at 12,000 g for 10 minutes.

11. Discard the supernatant and resuspend the pellet of inclusion bodies in 1 ml of 1M urea. Incubate for 30 minutes at 37° C. Spin 10 minutes in microfuge at 12,000 g.

12. Repeat step #11 twice.

13. Each pellet of the inclusion bodies is then dissolved in 200 µl of Laemmli sample buffer and analyzed by SDS-PAGE. Alternatively, resuspend inclusion body pellets in 600 µl of buffer C to solubilize the recombinant CRIPTO protein.

Recombinant CRIPTO Protein Characterization

Figure 2:
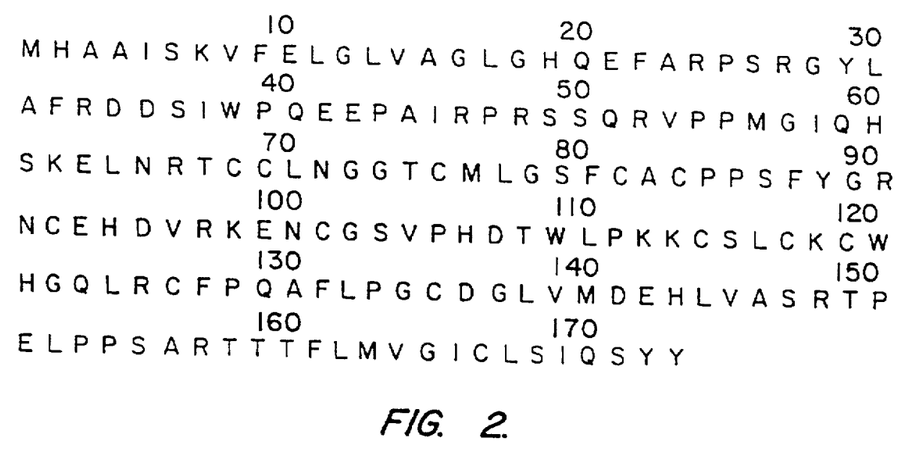
FIG. 2 shows the amino acid sequence of the human CRIPTO protein as it is recombinantly produced in E. coli.

1. The CRIPTO cDNA is used to produce a recombinant CRIPTO protein in *E. coli* as described above. The amino acid sequence of the CRIPTO protein is shown in FIG. 2. The inclusion body pellets are resuspended in 600 µl of buffer C and incubated at 37° C. for 18 hours to achieve almost 100% solubilization of the CRIPTO protein.

2. A partial solubilization is achieved in either 0.1M Tris-HCl buffer (pH 8.0) containing 6M guanidine HCl, 10M reduced glutathione and 1M oxidized glutathione or in 0.05M Tris-HCl buffer (pH 8.0) containing 1mM EDTA, 0.1M NaCl, 8M urea diluted with nine volumes of 0.05M $KH_2PO_4$ (pH 10.7), 1 mM EDTA (pH 8.0) and 0.05M NaCl.

3. Following solubilization and SDS-PAGE analysis, the CRIPTO protein has a Mr of about 20,000 to 22,000.

A deposit of the cloned cDNA of the CRIPTO gene has been made at the ATCC on Feb. 28, 1990 under accession number 61412. The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially pure" as used herein means as pure as can be obtained by standard isolation and purification techniques conventionally known to one of ordinary skill in the art.

The term "a reactive amount" as used herein means a quantity of the protein that would function in a manner desired in a particular application or utility of the protein.

As mentioned above, CRIPTO is transcribed into 2200 nucleotide long mRNA which is translated into a protein of 188 amino acid residues. Table 1 shows the expression of CRIPTO gene in humans and mice. The gene is active in teratocarcinoma cells, but inactive both in normal and other transformed cells and shut off when the teratocarcinoma cells are induced to differentiate by retinoic acid.

Figure 3:
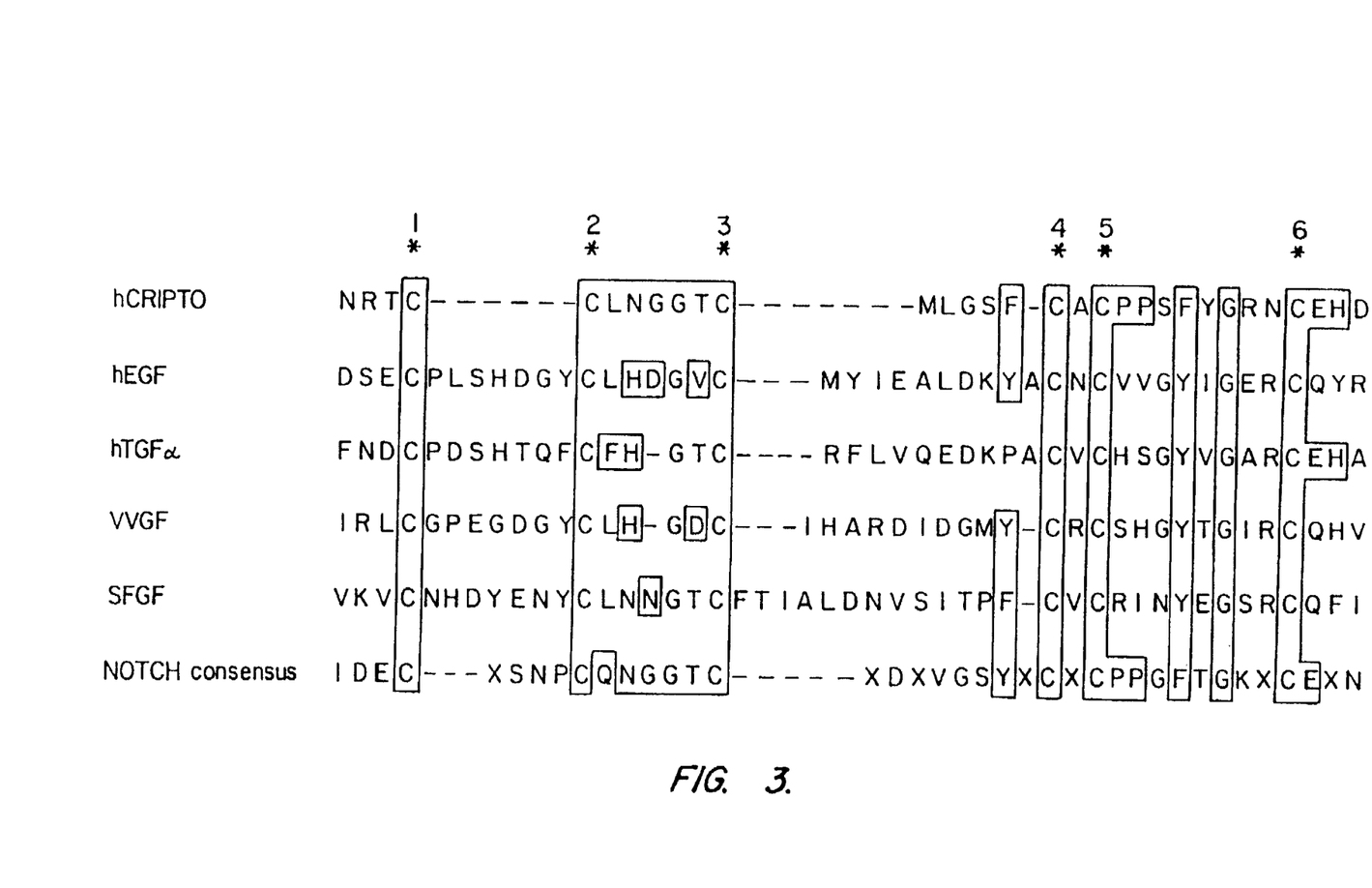
FIG. 3 is a comparison of the amino acid sequence of the human CRIPTO gene to several prior art proteins.

The amino acid sequence of CRIPTO protein was screened against a representative protein sequence database (Microgenie, Beckman). This search revealed that the CRIPTO protein is similar to several proteins, some of which are shown in FIG. 3. The similarity is restricted to a ~40 amino acid long, cysteine-rich, sequence known as the EGF-like segment. Besides the six cysteine residues in the characteristic spatial array, other amino acids are conserved among these proteins, e.g. the glycine, phenylalanine and tyrosine residues boxed in FIG. 1.

Transforming Potential of the CRIPTO gene

It has been shown that certain oncogenes, such as K-FGF, c-sis, proto-dbl and c-erbB-2 can transform murine fibroblasts when their expression is driven by a strong promoter. Similarly, TGFα and EGF genes under the control of a strong promoter can induce transformation and tumorigenicity in fibroblasts.

Figure 4:
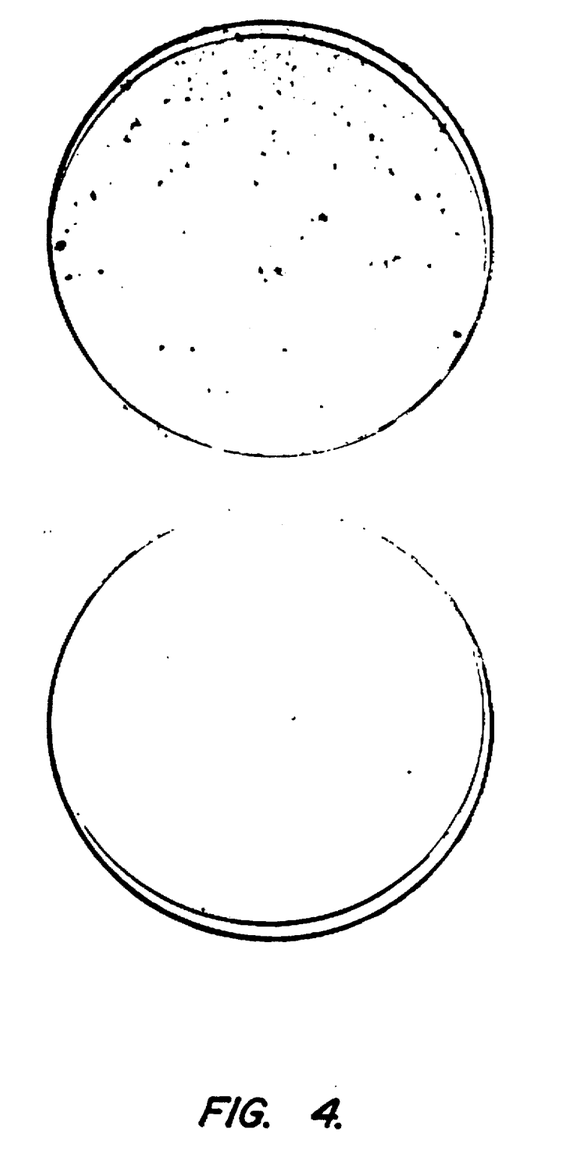
FIG. 4 demonstrates the focus forming activity of the human gene when transfected into NIH 3T3 cells.

To investigate whether the human CRIPTO gene has these properties, its cDNA was introduced into an expression vector in which transcription is controlled by the RSV long terminal repeats (LTR) (Gorman et al, 1982). The construct was transfected into NIH3T3 cells and its focus-forming activity was monitored (FIG. 4). In this experiment, the CRIPTO cDNA induced foci of transformed cells at an efficiency of 600 focus-forming units per pmol of DNA.

When CRIPTO cDNA was placed into a retroviral expression vector plasmid and transfected into mouse NIH-3T3 fibroblasts and into mouse NOG-8 mammary epithelial cells, in both of these cell types overexpression of this gene resulted in the in vitro transformation of these cells. (Tables 2 and 3).

As indicated above, substantially pure, isolated, recombinant CRIPTO protein (rCRIPTO) was obtained from a baculo virus expression vector in which the CRIPTO cDNA had been integrated. The availability of the CRIPTO cDNA and rCRIPTO protein now make it possible to detect cells or tissues expressing the CRIPTO gene. Various utilities of the CRIPTO cDNA and CRIPTO protein are now described.

Application and utilities of the CRIPTO cDNA and CRIPTO protein

Figure 5:
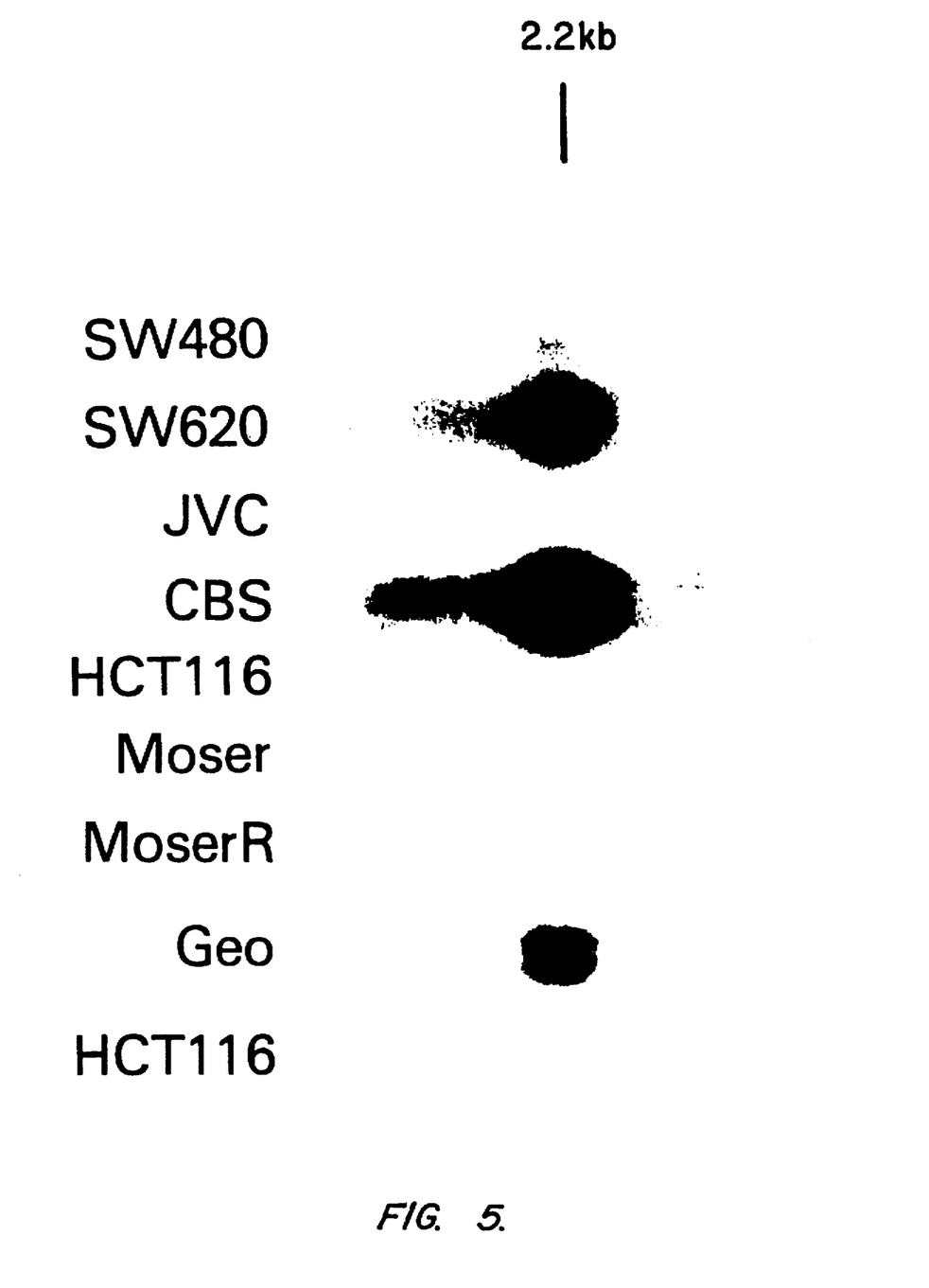
FIG. 5 is a Northern blot showing expression of the CRIPTO gene by various human colon tumor cell lines.
Figure 6:
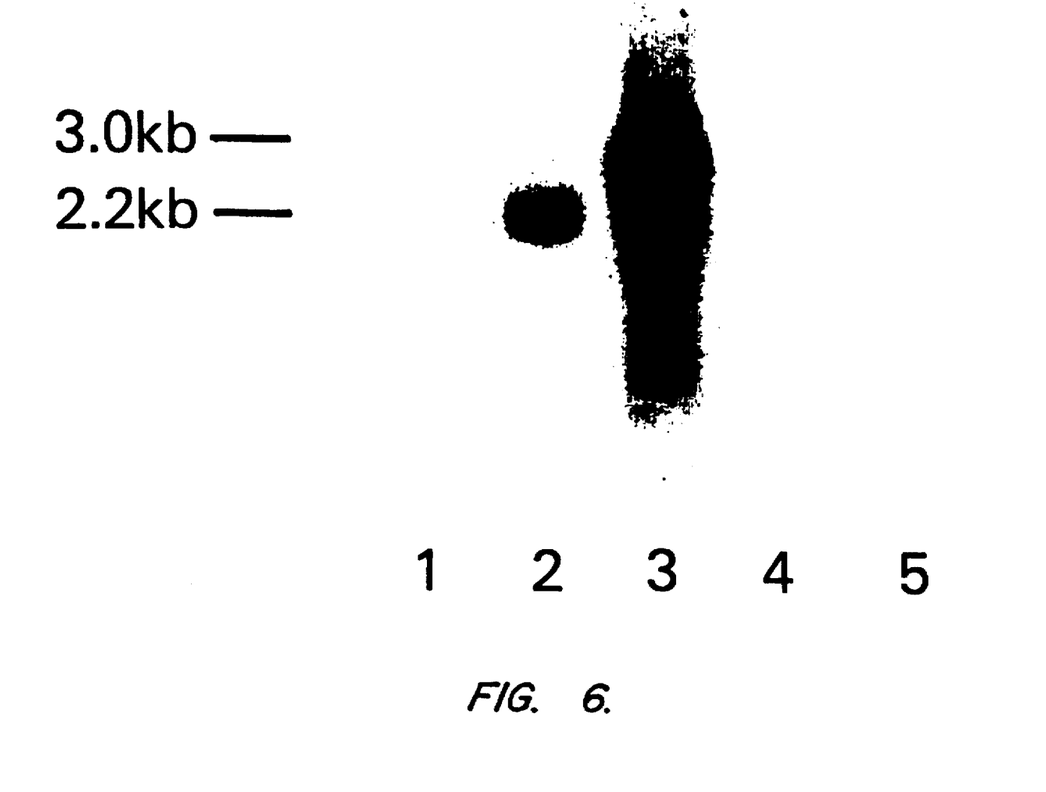
FIG. 6 is a Northern blot demonstrating that the CRIPTO gene is not expressed in normal human colon tissue.

Since the mRNA for the CRIPTO gene is expressed in approximately 60% to 70% of human colon tumor cell lines and at an equal frequency in primary human colon tumors, but not in normal human colon tissue (see Northern blot FIGS. 5 and 6), therefore, expression of CRIPTO mRNA and CRIPTO protein in a tissue would be a major tumor specific marker for the diagnosis and eventual prognosis of different types of cancer such as colorectal cancer. In addition, the CRIPTO gene maps to human chromosome 3 potentially at a region where deletions frequently occur and where such deletions have been found to be associated with a subset of primary human breast tumors and with a majority of small cell lung carcinomas. Hence, a loss of heterozygosity for this gene and/or a loss of or a reduction in CRIPTO mRNA expression due to deletions of one or both alleles of the CRIPTO gene may serve as adjunct tumor specific markers for other types of human cancer. Additionally, it has been experimentally demonstrated that introduction and subsequent overexpression of the human CRIPTO gene in a retroviral expression vector can lead to the in vitro transformation as detected by focus-forming activity or by anchorage-independent growth in soft agar of mouse NIH-3T3 fibroblast cells and of mouse NOG-8 mammary epithelial cells (Tables 2 & 3) indicating a role of this gene in the neoplastic process. Based on these facts, the availability of the CRIPTO cDNA and recombinant CRIPTO protein now allows the following applications:

1. The molecularly clones, full-length human CRIPTO cDNA can be nick-translated, isotopically labeled, for example, with $^{55}P$ nucleotides and subsequently used as a probe for the analysis of Southern blots containing endonuclease digested DNA preparations to ascertain if there are amplifications, rearrangements, deletions or restriction fragment length polymorphisms of the CRIPTO gene in normal versus tumor tissue.

2. The labeled nick-translated CRIPTO cDNA can also be utilized for the analysis of Northern blots that contain poly(A)+RNA to determine the relative levels of CRIPTO mRNA expression in various normal and pathologic tissue samples.

3. The CRIPTO cDNA can be cloned into an SP6/T7 pGEM expression vector and the like and can then be used to generate a corresponding cRNA antisense riboprobe. This antisense riboprobe could then be labeled with $^{55}S$ nucleotides and utilized as a suitable probe for in situ RNA:RNA hybridization for histologic localization in normal or pathologic cells expressing CRIPTO mRNA.

4. CRIPTO sense oligonucleotides can be chemically synthesized and can be used as appropriate probes in a polymerase chain reaction (PCR) for potential detection of low levels of CRIPTO mRNA and for amplification of CRIPTO genomic sequences for subsequent isolation and cloning.

5. The CRIPTO cDNA can be utilized to generate either expression vector plasmids for transfection or to generate replication defective recombinant ecotropic or amphotropic retroviral expression vectors for infection into cells for determining whether overexpression of this gene in vitro might lead to malignant transformation or might alter the growth or differentiation properties of different mammalian cell types.

6. The CRIPTO cDNA when placed in an appropriate expression vector plasmid or in a comparable retroviral expression vector in the opposite orientation can be used to generate antisense mRNA. Such antisense expression vectors can then be used to transfect or to infect normal and malignant cells in vitro in order to determine whether endogenous CRIPTO expression is important in maintaining the proliferation, differentiation or transformation of these cells.

7. Nonderivatized or thio-derivatized CRIPTO antisense oligonucleotides can be chemically synthesized and used to treat cells in vitro similarly as described in #6 above. Additionally, antisense CRIPTO oligonucleotides can be incorporated into liposomes for site-directed delivery in vivo to tumors when appropriate tumor-specific monoclonal antibodies are also incorporated into these same vesicles.

8. The CRIPTO cDNA can be placed into various bacterial, yeast, insect baculo virus or mammalian expression vectors in order to obtain sufficient quantities of a potentially biologically active, recombinant CRIPTO protein.

9. A recombinant CRIPTO protein can be used to generate a panel of polyclonal (in rabbits, sheep, goat or pigs) and mouse monoclonal antibodies such that these immunological reagents can be used to screen for CRIPTO protein expression in normal and pathologic human and animal tissue samples by immunocytochemistry, by Western blot analysis, by enzyme-linked immune substrate assay (ELISA), by radioimmunoassay (RIA) and the like.

10. Since the CRIPTO protein is a member of the epidermal growth factor (EGF) supergene family that contains a variety of peptide mitogens and growth inhibitors, a biologically active recombinant CRIPTO protein can be used to determine if this peptide has any growth regulatory activity on a variety of normal and tumor cells in vitro.

11. Additionally, a recombinant CRIPTO protein can be iodinated and can be utilized to identify and characterize specific cell surface receptors for this potential growth modulatory peptide using conventional chemical cross-linking techniques.

It is noted that the methodologies for the above noted utilities are well known to one of ordinary skill in the art and no novel techniques are seen involved in making such usages. A composition of matter, in accordance with the present invention, comprises a reactive amount of the rCRIPTO protein in a sterile, non-toxic carrier or vehicle.

It is understood that the examples and embodiments described herein are for illustrative purposes only and that various modifications or changes in light thereof will be suggested to persons skilled in the art and are to be included within the spirit and purview of this application and scope of the appended claims.

TABLE I

EXPRESSION OF CRIPTO GENE IN HUMANS AND MICE

|  | Total RNA | Poly(A)+ RNA |
|---|---|---|
| Organs and tissues |  |  |
| Placenta (human) | − | − |
| Testis (mouse) | − | − |
| Cell lines |  |  |
| HL60 (undifferentiated human myeloid cells) | − | ND |
| JEG (human choriocarcinoma cells) | − | − |
| PA-1 (human neuroblastoma cells) | − | ND |
| Ca-Ma (human mammary carcinoma cells) | − | ND |
| Human T lymphocyte | − | ND |
| HeLa | − | − |
| NA43 (human fibroblasts) | ND | − |

TABLE I-continued

EXPRESSION OF CRIPTO GENE IN HUMANS AND MICE

|  | Total RNA | Poly(A)+ RNA |
|---|---|---|
| NT2D1 (undifferentiated human teratocarcinoma cells) | + | + |
| ΔNT2D1 (differentiated human teratocarcinoma cells) | − | − |
| Term placenta fibroblasts | ND | − |
| Term placenta primary culture | ND | − |
| F9 (undifferentiated mouse teratocarcinoma cells) | + | ND |
| ΔF9 differentiated mouse teratocarcinoma cells) | − | ND |
| NIH3T3 (mouse fibroblasts) | − | ND |

ND, Not determined

TABLE 2

Anchorage-Independent Growth of Mouse NOG-8 Mammary Epithelial Cells Transfected with a Human cripto cDNA in a RSU Ehpression Vector Plasmid

| Clone | Total number of colonies/dish |
|---|---|
| NOG-8 (parental nontransfected) | 10 ± 5* (−) |
| 2E | 1690 ± 80 (+++) |
| 2L | 925 ± 70 (++) |
| 2F | 175 ± 25 (+) |
| 2H | 166 ± 10 (+) |

*$2 \times 10^4$ cells were seeded in 0.3% soft agar over a 0.8% agar overlay in 35 mm tissue culture dishes. Cultures were maintained for 14 days prior to staining of the cells with nitroblue tetrazolium. Colonies greater than 50 μm were scored and counted on an Artek colony counter. Results are the average from four separate dishes ± S.D. Numbers in parenthesis represent relative amounts of cripto mRNA as detected in cells following Northern blot hybridization with a labeled human cripto cDNA insert.

TABLE 3

Focus-Forming Activity of Human cripto cDNA in a RSU Ehpression Vector Plasmid after Transfection into Mouse NIH-3T3 Cells

| Clone | Total number of foci/dish |
|---|---|
| NIH-3T3 (parental nontransfected) | 5 ± 2* |
| Clone γ9 | 82 ± 5 |

*$2 \times 10^3$ cells were seeded in 35 mm dishes and maintained for 2 weeks prior to staining with crystal violet.

What is claimed is:

1. An antibody that specifically binds a CRIPTO protein having an amino acid sequence shown in FIG. 2.

2. An antibody of claim 1, wherein said antibody is polyclonal.

3. An antibody of claim 1, wherein said antibody is monoclonal.

4. A method for screening for expression of a CRIPTO protein in a tissue sample, comprising the following steps:

contacting the tissue sample with an effective amount of the antibody of claim 1;

detecting binding of the antibody to the expressed CRIPTO protein.

* * * * *